United States Patent [19]

Phelan et al.

[11] 4,397,186

[45] Aug. 9, 1983

[54] COAXIAL DIRECT-COUPLED ULTRASONIC PROBE AND METHOD OF NON-DESTRUCTIVE TESTING

[75] Inventors: Charles S. Phelan, Tustin; Jacob R. Fort, El Toro, both of Calif.

[73] Assignee: Shur-Lok Corporation, Irvine, Calif.

[21] Appl. No.: 243,140

[22] Filed: Mar. 12, 1981

[51] Int. Cl.³ ............................................ G01N 29/04
[52] U.S. Cl. ........................................ 73/584; 73/624
[58] Field of Search .................. 73/584, 588, 579, 582, 73/620, 624, 627, 628, 629, 632, 633, 641, 662

[56] References Cited

U.S. PATENT DOCUMENTS

| | | | |
|---|---|---|---|
| 2,458,771 | 1/1949 | Firestone | 73/629 |
| 2,601,779 | 7/1952 | Firestone | 73/632 |
| 2,784,325 | 3/1957 | Halliday et al. | 73/628 |
| 2,989,864 | 6/1961 | Bamford | 73/620 |
| 3,320,796 | 5/1967 | Darby | 73/576 |
| 3,958,450 | 5/1976 | Kleesattel | 73/579 |

FOREIGN PATENT DOCUMENTS 461355  4/1975  U.S.S.R. .................. 73/632

*Primary Examiner*—Stephen A. Kreitman

*Attorney, Agent, or Firm*—Knobbe, Martens, Olson & Bear

[57] ABSTRACT

An improvement to ultrasonic probes useful in the non-destructive testing of structural materials includes a compact, high-sensitivity coaxial design probe. The probe has a centrally located transmitter point and a circumferentially arranged receiver ring. The geometrical relationship between the transmitter point and the receiver ring provides for high-sensitivity in the detection of defects and allows for a compact construction without orientational sensitivity. A receiver tube is provided which encloses the probe and acts as a tuned wave guide for the detection of ultrasonic vibrations from the structural material under test. The increased sensitivity of the improved ultrasonic probe is advantageous in the testing of non-metallic structural materials having a complex composite structure. The compactness of the improved ultrasonic probe is advantageous in the testing of structural materials having complex and narrow shapes. The improved probe includes a transmitter assembly slidably mounted inside a receiver tube and spring biased to project from the receiver tube. The receiver tube includes an internally mounted separator wall which is acoustically coupled to a receiver transducer so that the receiver transducer is mounted behind the transmitter assembly.

15 Claims, 10 Drawing Figures

COAXIAL DIRECT-COUPLED ULTRASONIC PROBE AND METHOD OF NON-DESTRUCTIVE TESTING

BACKGROUND OF THE INVENTION

This invention relates generally to devices for locating flaws or defects in structural materials and pertains more particularly to electronic probes for measuring the progation of ultrasonic acoustic waves through structural materials.

A problem faced by manufacturers of structural materials is the need to provide materials which can be relied on to meet specified performance criteria such as strength and fatigue resistance. In order to insure that such criteria are met, a method of testing is often used. For very expensive structural materials and materials used for applications in which structural failure would be catastrophic, a non-destructive testing technique must be used in order to insure that each structure produced is sound. For example, expensive structural materials in the framework of an aircraft must be tested in order to insure that the aircraft does not come apart in flight.

It is important that non-destructive testing techniques be capable of evaluating the soundness of all sizes and shapes of structural materials in use. Typically, such testing is used to decide whether a structural material having a defect or flaw in it should be replaced. The testing may be performed at the time that the structural material is fabricated and may also be performed in the field periodically to locate defects which may develop with time.

Structural materials which are candidates for non-destructive testing may include metals such as aluminum, titanium, and stainless steel which may be electrically conductive or may be substantially non-conductive electrically. Structures composed of non-metals such as boron graphite which is electrically conductive may be candidates for non-destructive testing. Non-metallic, electrically non-conductive materials such as fiberglass or graphite composites are popular structural materials which are candidates for non-destructive testing. A popular composite structural material now in use includes aramid fibers.

Structural materials in common use are formed as relatively homogeneous solids, as laminated solids with cross-plys, and as honeycomb or corrugated structures. A particular objective in non-destructive testing is to locate voids or defects in adhesive bonding between layers inside laminated solids. Such laminated solid structural materials are fabricated by bonding together sheets of material, such as resin impregnated fiberglass, with adhesives. Voids or defects may result in such laminated structural materials where the adhesive has failed or where adhesion has been prevented by water or other contaminants.

A particular type of structural material which has recently become popular is a composite material composed of a matrix of aligned, elongated graphite fibers embedded in a resin and which is substantially non-conductive electrically. Such materials are commercially available under the trademarks "Rhordyne" (from Rohr Industries) and "Kevlar" (from DuPont). Parts made from structural materials with aligned graphite fibers are characterized by low mass, high strength, and strength maximized and concentrated in preselected directions and areas. Structural materials containing aligned graphite fibers are candidates for non-destructive testing to locate graphite fibers which are misaligned and to find defects where the graphite fiber matrix is distorted or irregular. The strength and performance of the structural materials containing aligned graphite fibers is very much dependent upon the uniformity and regularity of the fiber matrix since the function of the matrix is to insure that the fibers cooperate together to mutually reinforce the structural material.

Structural materials which are candidates for non-destructive testing are fabricated into parts used for fixed and rotary structures, control surfaces, fairings, fuselage skin bonded lap joints, rotary wing blades, root stiffener sections, anti-erosion or ablative coatings, and aircraft interior paneling and floor structures. Such parts often have elaborate and precisely convoluted shapes with narrow openings and curved surfaces. Parts which are very expensive or designed for functions requiring high reliability, are particularly candidates for non-destructive testing.

A prior method used in the non-destructive testing of electrically conductive structural materials involves the use of a magnetic field to induce eddy currents in the structural material to be tested. The induced eddy currents produce mechanical acoustical vibrations in the structural material, which, in accordance with the prior method, are detected by a microphone.

Another prior method used in the non-destructive testing of structural materials involves transmitting mechanical acoustical vibrations into the structural material at a narrow end or point. As above, the mechanical acoustic vibrations passing through the structural material are detected in this prior method by a microphone which may be coupled to the structural material through a receiver point contact spaced apart from the transmitter point. In this prior method, a known technique for reducing noise and crosstalk errors is to measure the second harmonic of the transmitted frequency.

A problem with the prior eddy current non-destructive testing method is that the method will not work with electrically non-conductive structural materials. A problem with the point contact method mentioned above is the lack of sensitivity to measure small defects or voids and to detect misaligned fibers or distortions in the fiber matrix of structural materials having aligned graphite fibers. Another problem with the point contact method is the orientational sensitivity of the method such that defects directly between the transmitter and receiver points may be detected but defects displaced from between the transmitter and receiver points may evade detection. In particular, such orientational sensitivity increases the likelihood that narrow, elongated defects will be overlooked. If the line between the transmitter and receiver points is not passed through the width of such a narrow, elongated defect, then the defect may well go undetected. Such orientational sensitivity gives rise to the requirement that a structural material be extensively scanned with the transmitter and receiver points in order to perform a complete test. A problem with both prior methods is that rather large probes are required which are not compatible with the intricate and demanding shapes of the structural materials to be tested.

In practice, testing with either the eddy current method or the point contact method involves scanning a probe over the surface of a structural material to tested and observing an electronic indicator device connected to the probe to display a reading indicative of the transmission of vibrations through the structural material. The usual technique for scanning the probe over the material surface is to make slightly overlapping loop passes.

SUMMARY OF THE INVENTION

The present invention relates to an ultrasonic probe for non-destructive testing in which the preferred embodiment of the probe has a central transmitter button for sending ultrasonic pulses into a test material, and further has a circular receiver ring surrounding the transmitter button for intercepting ultrasonic vibrations passing through the test material. A significant feature provided by the probe construction of this invention is a small physical probe size allowing the probe to fit into narrow openings in structural materials to be tested. An important benefit provided by probes constructed in accordance with this invention is omnidirectional response sensitivity which makes possible the use of fewer search passes of the probe over the structural material in performing a systematic non-destructive testing search for defects. Such omnidirectional response sensitivity further provides advantages in insuring the reliable detection of defects or voids regardless of the relative physical orientation between the defect and the probe, and in insuring that narrow, elongated defects are not overlooked by the probe.

The ultrasonic probe of the preferred embodiment of this invention further has a transmitter driver positioned behind the transmitter contact, and a receiver transducer mounted behind the transmitter driver and connected to the receiver ring through a receiver contact. An advantage enjoyed by the construction of the preferred embodiment is a high sensitivity to the presence of defects and misalignments in the structure of materials under test. The receiver tube of this invention acts both as a conduit for ultrasonic vibrations and as a support lending structural rigidity to the probe itself. The receiver tube also includes an internal separator wall which enhances the vibration and defect detecting performance of the probe.

Probes constructed in accordance with this invention may exhibit both a high performance and a compact size so that demanding new types of materials and shapes of parts may be adequately and reliably tested.

DESCRIPTION OF THE PREFERRED EMBODIMENT

Figure 1:
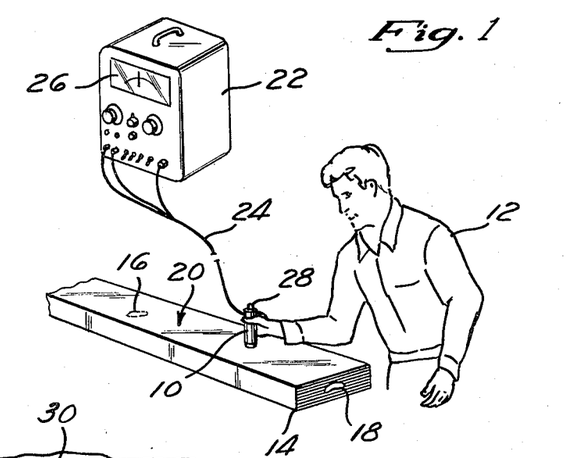
FIG. 1 is a perspective view showing the ultrasonic probe of this invention, structural material under test, an electronic test set, and a user holding the ultrasonic probe.

Referring first to FIG. 1, the ultrasonic probe 10 is handheld by the user 12 in order to check the structural material 14. The purpose of ultrasonic probe 10 is to identify the locate voids, defects, or imperfections in structural material 14 as illustrated by defects 16 and 18. In practice, the user 12 scans the probe 10 over the surface 20 of structural material 14 in order to detect defects within structural material 14.

Probe 10 is connected to electronic test set 22 by a cable 24. Test set 22 includes a moving needle analog meter 26 which visually indicates the measurements made by test set 22. In practice, user 12 observes meter 26 to note changes in meter 26 as probe 10 is moved over surface 20. Changes in meter 26 indicate to user 12 that probe 10 has been moved over a defect within the structural material 14. Probe 10 is further equipped with a lamp 28 mounted thereon which is controlled by test set 22 to emit light in response to the detection of defects within the structural material 14.

Probe 10 is compact in size to fit the hand of user 12 and to fit into narrow openings (not shown) which may be present in structural material 14. Thus, probe 10 is compatible with the intricate and demanding shapes that structural material 14 may have, such as elaborate and precisely convoluted shapes with narrow openings and curved surfaces.

Figure 2:
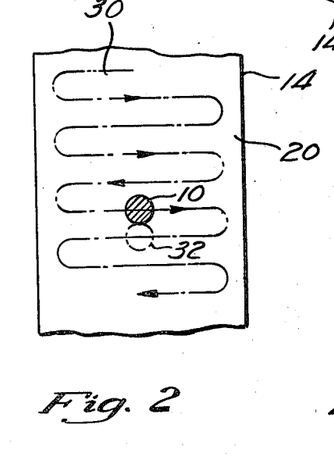
FIG. 2 is a top overhead plan view of the ultrasonic probe of this invention on a structural material under test showing the loop passes used in scanning the ultrasonic probe over the surface of the structural material, and further showing the ultrasonic probe of this invention in a phantom position.

Referring next to FIG. 2, from an overhead plan view, the outline of probe 10 is circular. The path 30 consists of non-overlapping loops on the surface 20 and along which the probe 10 is moved during testing. By following the path 30, probe 10 completely covers the surface 20 of material 14 in slightly overlapping search passes while performing a systematic non-destructive testing search for defects in material 14. The arrows shown on path 30 indicate the direction of movement of probe 10. Probe 10 is shown in phantom at 32 to illustrate that the distance between loops on path 30 allows the path 30 search passes to slightly overlap. In practice, probe 10 is manually passed over the structural material 14 along the path 30, which is not expressly laid out, but which is visualized or imagined by the user (not shown) of probe 10.

The omnidirectional sensitivity of probe 10 allows the path 30 to be relatively simple and avoids the need to follow a longer criss-cross or other type of tortuous path. Thus probe 10 allows reliable detection of defects or voids regardless of the relative physical orientation between the probe 10 and the defect or void. Also, the omnidirectional sensitivity of probe 10 insures that narrow, elongated defects are not overlooked when the search path 30 is used.

Figure 3:
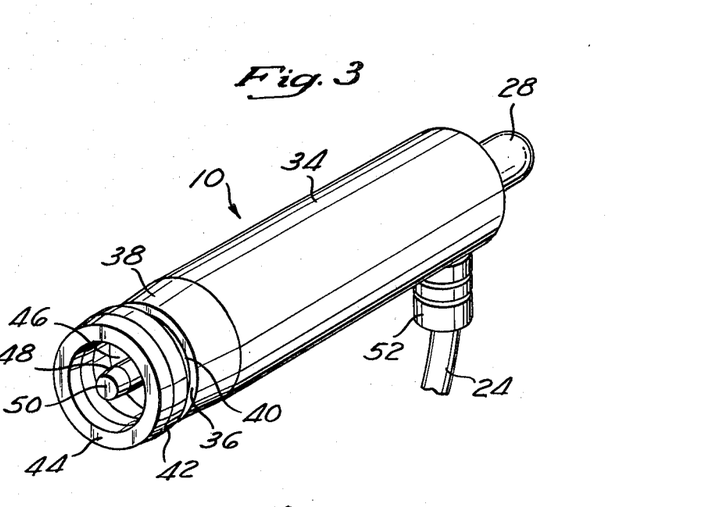
FIG. 3 is a front three-quarter perspective view of the ultrasonic probe of this invention.

Referring next to FIG. 3, probe 10 includes an elongated, tubular outer jacket 34 with a straight inner bore 36 and a tapered forward end 38. Jacket 34 is preferably composed of an electrically insulating and anti-static material such as polycarbonate or polystyrene and is shaped to be grasped by the hand of a user (not shown). A receiver tube 40 is tightly, slidably mounted inside bore 36 and projects from the forward end 38 of the outer jacket 34. A receiver ring 42 is generally toroidal in shape and is mounted on the forward end of the receiver tube 40. Receiver ring 42 is preferably composed of a wear-resistant metal such as stainless steel, but may be composed of a scratch preventing material, such as Teflon brand plastic material. The outer diameter of receiver ring 42 is preferably minimized to allow probe 10 to fit into narrow openings in structural materials to be tested. Receiver tube 40 is preferably composed of a metal such as aluminum. Receiver ring 42 has a receiver contact 44 which is the forward surface of ring 42 for physically contacting the surface 20 of structural material 4 (see FIG. 1).

A transmitter assembly 46 is slidably mounted coaxially inside receiver tube 40 and has a transmitter button 48 mounted at the forward end thereof. Transmitter button 48 is preferably a wear-resistant metal such as stainless steel, but may be composed of a scratch preventing material, such as Teflon brand plastic material. Transmitter button 48 has a transmitter contact 50 which is the forward surface of button 48 for physically contacting the surface 20 of structural material 14 (see FIG. 1).

The receiver contact 44 is positioned to surround and encircle the transmitter contact 50 when the probe 10 is brought into contact with the surface 20 of structural material 14. Thus, the receiver ring 50 operates in a highly effective manner to intercept mechanical vibrations resulting in the structural material 14 due to vibration of the transmitter button 48.

As used herein, the term omnidirectional response sensitivity refers to the sensitivity of the probe 10 of this invention to detect defects in substantially all radial directions outward from the transmitter button 48. The omnidirectional sensitivity of probe 10 is facilitated by receiver ring 42 which is preferably circular in shape.

A strain relief 52 is mounted on the outer jacket 34 and serves to protect and surround the cable 24 at the point where cable 24 enters inside the probe 10.

Figure 4:
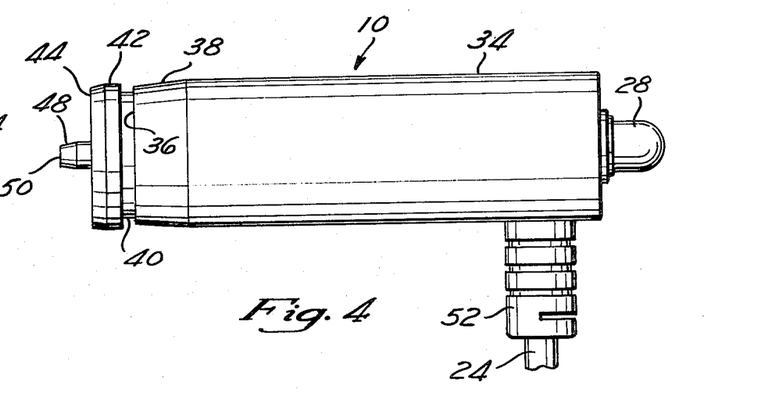
FIG. 4 is a side view of the ultrasonic probe of this invention.

Referring next to FIG. 4, when probe 10 is not placed in contact with structural material 14, transmitter button 48 is spring biased to protrude from the forward end of probe 10, beyond the receiver ring 42.

Figure 5:
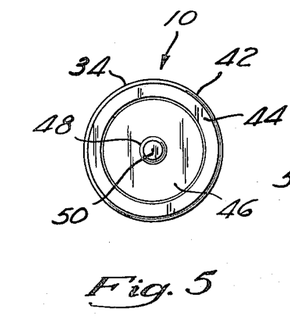
FIG. 5 is a front view of the ultrasonic probe of this invention.

Referring next to FIG. 5, the transmitter contact 50 is a surface region which is circular in shape. The receiver contact 44 is a surface region which has the shape of a circular strip or ring which surrounds or encircles the transmitter contact 50. Transmitter button 48 is coaxial with the outer jacket 34 and the receiver ring 42. The outside diameter of the outer jacket 34 is not substantially larger than the outside diameter of the receiver ring 42. In the preferred embodiment, the transmitter button 48 has a diameter of approximately 0.25 inches, and the receiver ring has an inside diameter of approximately 0.885 inches and an outside diameter of approximately 1.135 inches.

Figures 6, 7, 8:
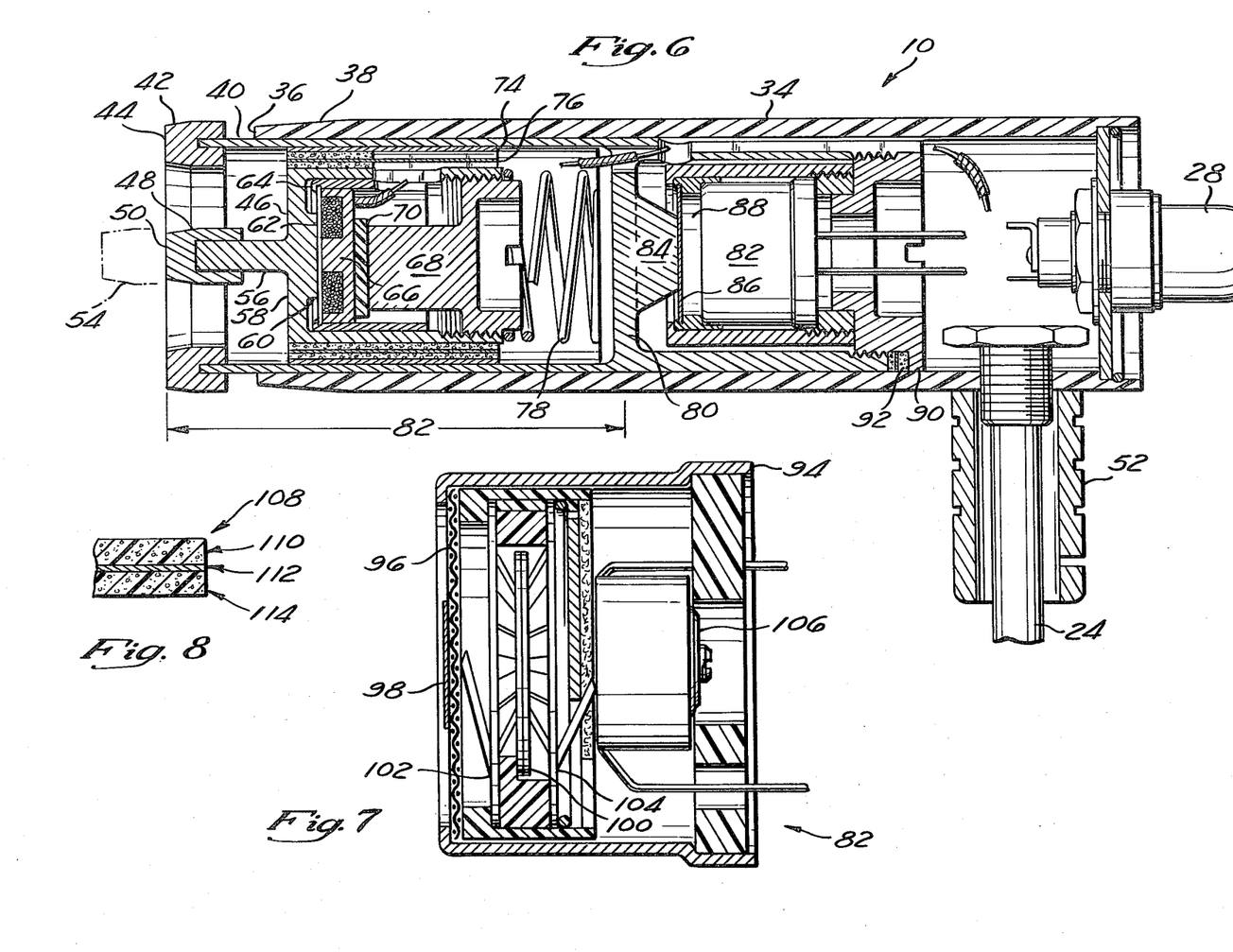
FIG. 6 is a partially cut away side view of the ultrasonic probe of this invention showing, in phantom, an extended position of the transmitter contact.
FIG. 7 is a partially cut away side view of the receiver transducer of the ultrasonic probe of this invention.
FIG. 8 is a cross-sectional view of sound dampening material used in the fabrication of the ultrasonic probe of this invention.

Referring next to FIG. 6, transmitter button 48 is shown in a retracted position in line with receiver ring 42; the retracted position corresponding to the location of transmitter button 48 when probe 10 is placed in contact with structural material 14 (see FIG. 1). Transmitter button 48 is shown in phantom at 54 in an extended position protruding from the forward end of probe 10, beyond the receiver ring 42; the extended position corresponding to the location of transmitter button 48 when probe 10 is not placed in contact with structural material 14 (see FIG. 1). The extended position shown in phantom at 54 corresponds to the position shown in FIG. 4.

The transmitter assembly 46 has the transmitter button 48 mounted on the prong 56 of the transmitter case 58. The transmitter case 58 is preferably composed of aluminum and shaped like a cylindrical cup with prong 56 extending outwardly from the base of the cup. Transmitter case 58 also has a vibration transferring projection 60 extending inwardly from the base of the cup, inside the cup.

A transmitter diaphragm 62 is preferably composed of tin plated steel, has a high coefficient of elasticity and makes contact with projection 60 to transfer vibrations to the transmitter case 58. The transmitter diaphragm 62 is swaged onto the transmitter support 64 which is preferably composed of aluminum, has the shape of a cylindrical sleeve, and slidably mounts inside the transmitter case 58. The diaphragm 68 is taughtly mounted on the support 64 and acts like a drumhead to vibrate readily.

The diaphragm 62 is caused to vibrate by a coil assembly 66 which has a coil of wire wound inside a standard, commercially available sintered ferrite cup core. The coil assembly 66 is forced in place against diaphragm 62 by transmitter retainer 68 which threadably mounts inside the cup of transmitter case 58. Transmitter retainer 68 is preferably composed of aluminum and is threadably adjustable to apply a preselected pressure on rubber pad 70 which bears against the coil assembly 66. Transmitter retainer 68 is adjusted so that coil assembly 68 bears tightly against diaphragm 62 but does not deform diaphragm 62. The transmitter assembly 46 also includes the diaphragm 62, transmitter support 64, coil assembly 66, transmitter retainer 68, and rubber pad 70.

A transmitter cushion 76 is attached to and surrounds the outside periphery of the cup of the transmitter case 58. Sliding guide 74 is preferably fabricated from a thin, cylindrical aluminum tube and is attached to and surrounds the transmitter cushion 76. The function of the guide 74 is to provide a smooth sliding surface so that transmitter assembly 46 may smoothly slide along the inside of the receiver tube 40. The function of transmitter cushion 76 is to act as a vibration dampener to impede the transmission of acoustic mechanical vibrations from the transmitter case 58, through the guide 74 and to the receiver tube 40. The transmitter assembly 46 is prevented from completely sliding out of the receiver tube 40 by the receiver ring 42 which projects inside the tube 40 to act as a stop. The transmitter cushion 76 and sliding guide 74 are parts of the transmitter assembly 46.

The function of coil assembly 66 is to produce an alternating magnetic field which causes diaphragm 62 to vibrate and transmit acoustical vibrations through projection 60 and prong 56 to transmitter button 48. Coil assembly 66 is connected by electrically conductive wires through cable 24 to test set 22 (see FIG. 1) which serves to electrically excite the coil of wire in assembly 66 and to produce an alternating magnetic field in the core of assembly 66. The acoustical vibrations caused by assembly 66 are transmitted into structural material 14 (see FIG. 1) for testing purposes.

Spring 78 is preferably a steel helical coil spring mounted between separator wall 80 and transmitter assembly 58. The function of spring 78 is to spring bias transmitter assembly 46 so that assembly 46 is pushed out from inside the receiver tube 40. The spring 78 acts to prevent transmitter button 48 from bouncing and losing physical contact with structural material 14 (see FIG. 1) when acoustical mechanical vibrations are produced by coil assembly 66.

A function of receiver tube 40 is to conduct acoustical vibrations from receiver ring 42 to the separator wall 80. Another function of receiver tube 40 is to encase the probe 10 and provide enhanced structural rigidity to the probe 10 itself. Separator wall 80 is a part of receiver tube 40 and is essentially a circular disk plug extending across the diameter of tube 40 inside the tube 40. The separator wall 80 is located at a distance denoted by the number 82 from the forward end of tube 40 along the inside length of tube 40. The distance 82 extends from the receiver contact surface 44 to the separator wall 80. The magnitude of distance 82 is chosen to make tube 40 a tuned acoustical waveguide for the received vibrations. In order that the sensitivity of probe 10 be large, it is important that the distance 82 be equal to an odd number of quarter wavelengths of the acoustical vibrations to be measured. In the preferred embodiment, the frequency of the acoustical vibrations to be measured is approximately 30 kilohertz. It is preferable that the distance denoted 82 be approximately equal to 2.0 inches.

The separator wall 80 acts as a tap on a mechanical transmission line formed by the receiver tube 40 and the receiver ring 42, and the wall 80 is positioned along the length of the tube 40 to be approximately located at a maxima of a standing wave on the tube 40 having the frequency of the acoustical vibrations to be measured. The receiver tube 40 and ring 42 thus act as a tuned transmission line or waveguide in which separator wall 80 is located in a position to selectively intercept acoustical vibrations having the frequency of the acoustical vibrations to be measured. The receiver tube 40 acts as a frequency selective filter to selectively detect in wall 80 the acoustical vibrations to be measured and to reject acoustical vibrations of other frequencies. In the preferred embodiment, the acoustical vibrations transmitted by transmitter button 48 have a frequency of approximately 15 kilohertz and the frequency of the acoustical vibrations to be measured is approximately 30 kilohertz. It is known in this art that the detection of vibrations at a harmonic of the transmitted frequency will improve the performance of an ultrasonic probe.

The separator wall 80 has a centrally located, rearwardly extending projection 84 which makes contact with a receiver diaphragm 86 similar in construction to the transmitter diaphragm 62. Ultrasonic vibrations are transmitted from the projection 84, through the diaphragm 86, through an air space 88, and to the receiver transducer 82. The receiver diaphragm 86 is forced against the projection 84 by the stabilizer 90 which threads into the bore of the receiver tube 40. The function of the air space 88 is to act as a resonating cavity for the tightly mounted diaphragm 86 so that the diaphragm 86 vibrates in response to vibrations transferred by projection 84. The function of receiver transducer 82 is to detect acoustical vibrations occurring in the air space 88 and to produce an electrical signal in response thereto. A sound dampening washer 92 is provided between the receiver tube 40 and the stabilizer 90 so that undesirable coupling of acoustical signals from the outer shell of tube 40 through the stabilizer 90 and to and the receiver transducer 82 does not occur.

Referring next to FIG. 7, receiver transducer 82 has an outer shell 94 with a woven screen 96 mounted in the forward end thereof. The shell 94 is preferably cylindrical in shape, and the screen 96 is preferably a flat, circular washer of woven metal strands. A circular masking tape disk 98 is adhesively mounted to the center of the screen 96.

The receiver transducer 82 includes a disk of piezo electric material 100 which is mounted between a pair of supporting rings 102 and 104. The disk 100 is preferably composed of a piezo electric crystalline material such as type PZT 5B lead zirconate titanate. Alternative materials for disk 100 may include barium titanate or rochelle salts. Disk 100 is positioned so that acoustic sound waves may pass through the woven screen 96 and cause disk 100 to be vibrated, thus producing an electrical potential between the support rings 102 and 104 which make electrical contact with opposite sides of disk 100. The support ring 102 makes electrical contact with the woven screen 96 and the shell 94. Support ring 104 makes electrical contact with a potentiometer 106. Potentiometer 106 is connected as a voltage divider so that the sensitivity of the receiver transducer 82 may be adjusted. The output signal of the receiver transducer 82 is produced between the wiper of the potentiometer 106 and the case 94 and is conveyed to the test set 22 by the cable 24 (see FIG. 1).

Referring next to FIG. 8, a detailed cross-sectional view of the material 108 used in the fabrication of the cushion 76 and the washer 92 (see FIG. 6) is shown. The material 108 is commercially available under the trademark "Sound Mat LF" from Soundcoat Company, Inc., 3002 Croddy Way, Santa Ana, Calif. 92704. The function of material 108 is to impede the transmission of acoustical vibrations. Material 108 is composed of a three layer sandwich including lead foil 112 having layers 110 and 114 of flexible, solid plastic foam mounted on both sides thereof.

Figure 9A:
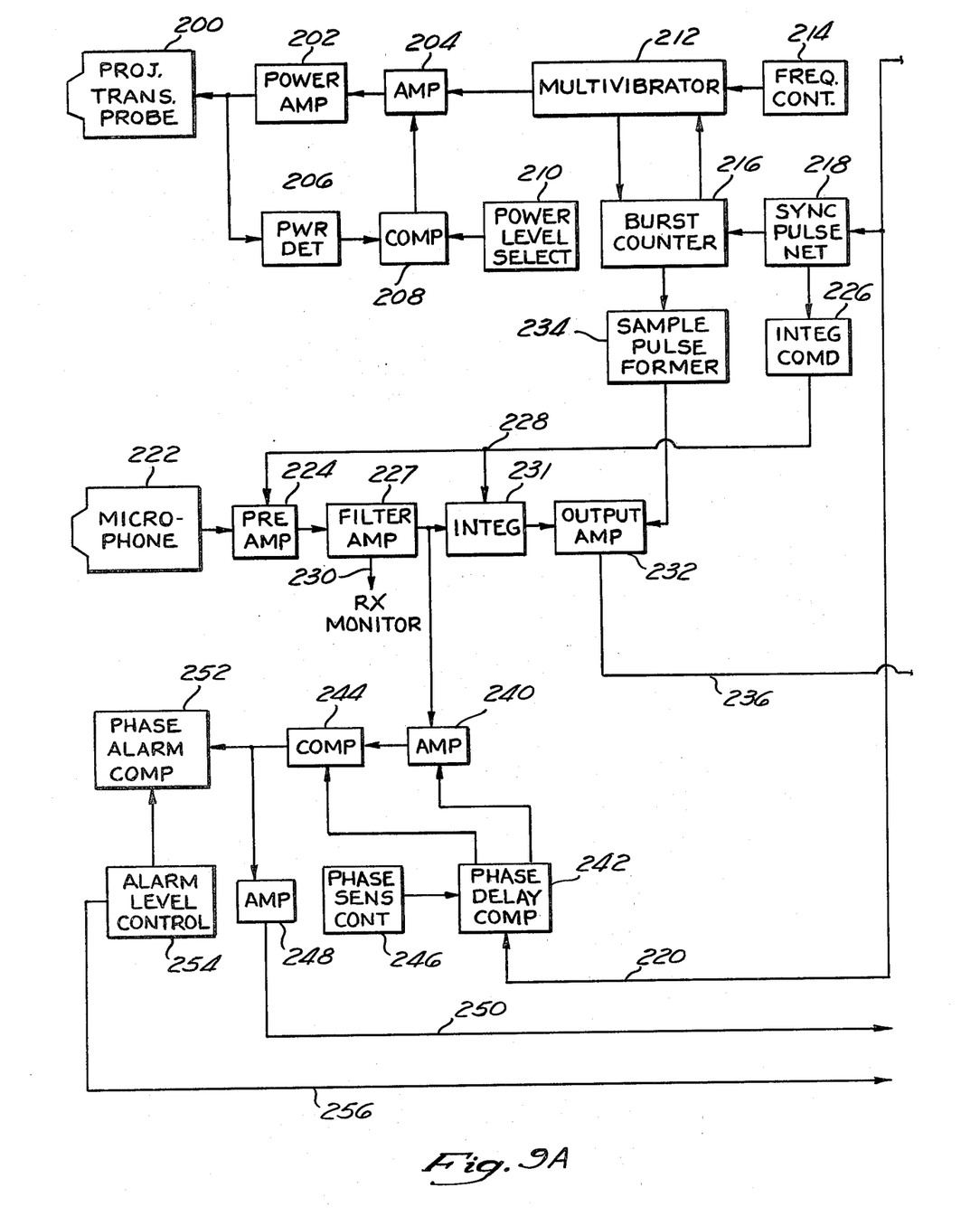
FIG. 9A is a block diagram of a portion of the electronic test set electrical circuitry for use with the ultrasonic probe of this invention.
Figure 9B:
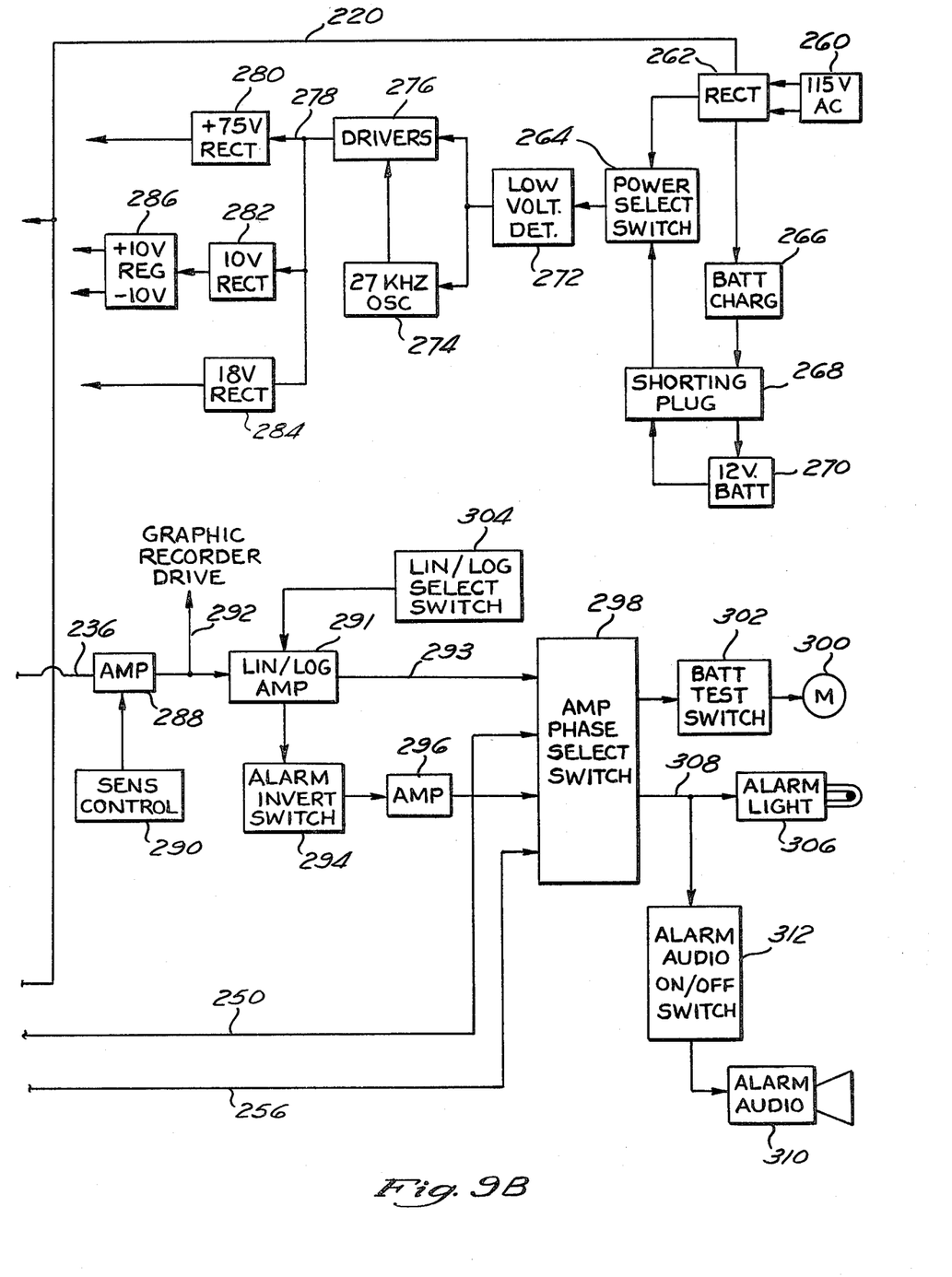
FIG. 9B is a block diagram of a portion of the electronic test set electrical circuitry for use with the ultrasonic probe of this invention, and FIGS. 9A and 9B taken together show the block diagram for the electronic test set electrical circuitry.

Referring next to FIG. 9A, the projector/transmitter probe 200 corresponds to the transmitter assembly 46 shown in FIG. 3. The circuitry shown in FIGS. 9A and 9B is the same type as has been used in the past with prior types of ultrasonic contacting and eddy current probes. Power to drive the probe 200 is provided by power amplifier 202 which is driven by an amplifier 204. A feedback loop consisting of a power detector 206 and comparator 208 is electrically connected around power amplifier 202 and amplifier 204 to measure the output of power amplifier 202 and to control the gain of amplifier 204. Comparator 208 serves to compare the measured output of power amplifier 202 with the preselected power level set by power level select 210. Power level select 210 corresponds to a manually adjustable knob on test set 22 (see FIG. 1) and is manually adjustable to accommodate the testing of the various sizes and compositions of structural materials to be tested.

Multivibrator 212 is an oscillator signal generator for producing approximately rectangular wave forms having a frequency of approximately 15 kilohertz. Frequency control 214 corresponds to a manually adjustable knob on test set 22 (see FIG. 1) and is electrically connected to multivibrator 212 to control the frequency of the oscillatory signal generated by multivibrator 212. The output of multivibrator 212 is connected to the input of amplifier 204 so that an amplified signal similar to the oscillatory signal produced by multivibrator 212 is presented to the probe 200. The function of multivibrator 212 is to produce the appropriate wave shape for properly exciting the probe 200.

Burst connector 216 is electrically connected to multivibrator 212 to control the operation thereof. Burst counter 216 causes multivibrator 212 to produce an output consisting of bursts of 15 kilohertz pulses, with each burst having 5 such pulses, and with the bursts occurring at a 60 hertz rate. Burst counter 216 controls the operation of multivibrator 212 by sensing the output signal formed by multivibrator 212, and by selectively turning multivibrator 212 on and off to produce the above described output waveform for multivibrator 212. Such an output signal consisting of bursts of 15 kilohertz pulses is transferred from multivibrator 212 through amplifiers 204 and 202 to drive the probe 200.

Synchronization pulse network 218 is connected between bus 220 and burst counter 216 to properly trigger burst counter 216 at a 60 hertz rate. Bus 220 is a source of 60 hertz triggering signals. Burst counter 216 cooperates with synchronization pulse network 218 so that after 5 pulses are generated by multivibrator 212, burst counter 216 turns multivibrator 212 off until a triggering pulse is received by burst counter 216 from network 218. Upon receipt of a triggering pulse by burst counter 216 from network 218, counter 216 turns multivibrator 212 on until 5 pulses are generated by multivibrator 212, at which time burst counter 216 turns multivibrator 212 off.

Microphone 222 corresponds to receiver transducer 82 (see FIG. 6). The function of microphone 222 is to detect the ultrasonic vibrations occurring in structural material 14 (see FIG. 1) caused by the projector/transmitter probe 200. The output of microphone 222 is electrically connected to preamplifier 224 which amplifies the electrical signal generated by microphone 222. The electrical signal generated by microphone 222 is responsive to the ultrasonic vibrations occurring in structural material 14 (see FIG. 1). The integration command controller 226 is connected to the network 218 and generates an integrate command signal on bus 228. Preamplifier 224 is connected to bus 228 so that controller 226 selectively controls preamplifier 224 to amplify the signals coming from microphone 222 only when a trigger pulse occurs on bus 220. Thus, a function of controller 226 is to insure that preamplifier 224 amplifies the signals coming from microphone 222 only when the projector/transmitter probe 200 is transmitting a burst of pulses.

Filter amplifier 227 is electrically connected to the output of preamplifier 224 and serves to amplify and filter the signal produced by preamplifier 224. Filter amplifier 227 also generates a receiver monitor output 230 which may be selectively displayed on the meter 26 of test set 22 (see FIG. 1). The purpose of generating output 230 is to allow the user 12 of this invention to determine the presence and intensity of the signal detected by microphone 222. Output 230 is selected for display on meter 26 on test set 22 as a part of the initialization procedures for test set 22, prior to the actual testing of structural material 14 for defects.

Integrator 231 is electrically connected to the output of filter amplifier 226 and is triggered in operation by bus 228. The function of integrator 231 is to integrate the intensity of the received signal starting at the time that a transmitted pulse burst is started. Output amplifier 232 is electrically connected to the output of integrator 231. Sample pulse former 234 is electrically connected between burst counter 216 and output amplifier 232. The function of sample pulse former 234 is to control the output amplifier 232 so that the output amplifier 232 is on only when a burst of pulses is being produced by probe 200. The output signal produced on bus 236 is directly related to the amplitude vibration response by the structural material 14 under test and is sensitive to the presence of defects in the structural material 14.

Phase delay comparator 242 is electrically connected to amplifier 240 and comparator 244. The input of comparator 244 is electrically connected to the output of amplifier 240, and the amplifier 240, comparator 244, and phase delay comparator 242 cooperate together to act as a phase sensitive detector to detect phase shifts in the received signal produced by the output of filter amplifier 226. Phase sensitivity control 246 is electrically connected to control the phase delay comparator 242 so that a manual adjustment of the time period over which a phase comparison is made by comparator 244 may be accomplished. Comparator 244 measures the phase shift (at some "nth" count cycle) in the signal from receiver transducer 222. The setting of control 246 determines at which cycle (the "nth" count cycle) the phase comparison is made. Phase sensitivity control 246 corresponds to a manually adjustable knob on the face of test set 22 (see FIG. 1). Phase delay comparator 242 is electrically connected to bus 220 so that a phase comparison is made only when a burst of pulses is produced by projector 200. This triggering of comparator 242 by bus 220 is for the purpose of avoiding unwanted noise in the circuitry.

The output of comparator 244 is an electronic signal sensitive to the phase response of the structural material 14 under test when exposed to bursts of pulses from probe 200. The output of comparator 244 is responsive to the presence and location of defects in the structural material 14 under test. The input of amplifier 248 is electrically connected to the output of comparator 244 and generates an output on bus 250. The function of amplifier 248 is to increase the magnitude of the output signal of comparator 244 and produce an output on bus 250. The output of comparator 244 is electrically connected to an input of phase alarm comparator 252. The function of phase alarm comparator 252 is to compare the output of comparator 244 with the output of alarm level control 254 and to cause the alarm level control 254 to produce an alarm signal output on bus 256 if the output of comparator 244 exceeds the output of alarm level 254. Alarm level control 254 corresponds to a manually adjustable knob on the face of test set 22 (see FIG. 1) and is manually adjusted by user 12 to a preselected level so that an alarm signal output on bus 256 is produced only for defects which produced an output in comparator 244 above a preselected magnitude.

Referring next to FIG. 9B, power source 260 is a source of alternating current electric power such as commonly available line power. Rectifier 262 rectifies the alternating current provided by power source 260 and provides direct current power to power select switch 264 and battery charger 266. The rectifier 262 also provides a source of pulses on the bus 220 which are equal in frequency to the frequency of the alternating current provided by source 260 (usually 60 hertz). A 12 volt battery 270 is connected to the power select switch 264 through a plug 268. The function of the 12 volt battery 270 is to allow the circuitry disclosed in FIGS. 9A and 9B to be operated portably in the field when the power source 260 is not available. The function of the power select switch 264 is to select between power provided by the power source 260 and power provided by the battery 270. When the circuitry is operated in the field and the power source 260 is not available, the pulses on bus 220 are provided by a signal generator (not shown) driven by the battery 270 to provide pulses at a 60 hertz rate. The function of battery charger 266 is to charge the battery 270 when the power source 260 is connected to the rectifier 262.

Low voltage detector 272 is connected to the output of power select switch 264 and corresponds to an indicator lamp on the face of test set 22 (see FIG. 1) which serves to indicate when the DC power provided to test set 22 is not sufficient to satisfactorily activate the circuitry shown in FIGS. 9A and 9B. Oscillator 274 and drivers 276 are connected to power select switch 264 through the low voltage detector 272. Oscillator 274 and drivers 276 function as a power inverter to convert the direct current power coming from power select switch 264 into alternating current power on bus 278. The rectifiers 280, 282, and 284 are connected to the bus 278 for the purpose of converting the alternating current power on bus 278 into direct current voltages for use by the circuitry shown in FIGS. 9A and 9B. Regulator 286 is connected to the output of rectifier 282 for the purpose of providing precisely controlled direct current voltages for use by the circuitry shown in FIGS. 9A and 9B.

The input of amplifier 288 is connected to bus 236 and serves to amplify the signal output by amplifier 232 (see FIG. 9A). Sensitivity control 290 is connected to amplifier 288 to control the gain of amplifier 288. Sensitivity control 290 corresponds to a knob on the face of test set 22 (see FIG. 1). The output 292 of amplifier 288 is connected to a jack (not shown) on test set 22 (see FIG. 1) and is provided for connection to a graphical recorder (not shown) for permanently recording the results of the testing of structural material 14 for defects. The output of amplifier 288 is also connected to the input of linear/logarithmic amplifier 291. The output of amplifier 291 appears on bus 292. Alarm invert switch 294 is connected to an output of amplifier 291. The function of alarm invert switch 294 is to allow an inverted mode to be selected in which an alarm is created at all times unless a defect is present and detected in structural material 14. Amplifier 296 is connected to the output of switch 294 and serves to amplify the magnitude of the signal produced by switch 294.

Amplitude/phase select switch 298 serves to place test set 22 in a phase sensitive or amplitude sensitive mode. Meter 300 is connected to switch 298 through battery test switch 302. Meter 300 corresponds to the meter 26 on test set 22 (see FIG. 1). The function of battery test switch 302 is to cause meter 300 to momentarily indicate the state of charge in the battery 270. A function of the switch 298 is to select between the display of an amplitude sensitive signal on bus 293 and a phase sensitive signal on bus 250 for display on meter 300. That is, the condition of switch 298 determines whether the deflection of meter 300 is related to an amplitude measurement or to a phase measurement. When switch 298 is activated so that meter 300 displays a deflection related to the amplitude of signals received by microphone 222, amplifier 291 may be adjusted with linear/logarithmic select switch 304 to control the magnitude of the display on meter 300. Typically, when large changes in the amplitude of the output of the amplifier 288 are encountered, amplifier 291 is placed in a logarithmic mode by switch 304 so that large changes in signal may be displayed on meter 300. Conversely, if only small changes are encountered in the output of amplifier 288, amplifier 290 may be placed in a liner mode by switch 304 so that such small signals may be satisfactorily displayed on meter 300.

Alarm light 306 corresponds to the indicator light 28 (see FIG. 1) and is electrically connected to the output bus 308 of switch 298. Audio alarm 310 is located inside test set 22 and is electrically connected to bus 308 through on/off switch 312. The function of alarms 306 and 310 is to alert the operator 12 that a defect has been detected. A function of switch 298 is to switch the bus 308 between connecting with bus 256 and the output of amplifier 296. When bus 308 is connected to bus 256, alarms 306 and 310 are selectively activited when the phase response of structural material 14 indicates that a defect is present. When bus 308 is connected to the output of amplifier 296, alarms 306 and 310 are selectively activited when the amplitude response of structural material 14 indicates that a defect is present.

It is anticipated that various changes may be made in the shape, construction and operation of the invention as disclosed herein without departing from the spirit of scope of the invention as defined by the following claims.

What is claimed is:

1. A coaxial direct-coupled ultrasonic probe for use with a test set in the non-destructive testing of a structural material; said probe comprising:
    a transmitter assembly having a transmitter button for contacting said structural material and for transmitting ultrasonic acoustical vibrations into said structural material;
    a receiver ring having omnidirectional sensitivity and substantially surrounding said transmitter button so as to intercept vibrations produced in said structural material by said transmitter button; said receiver ring allowing the detection of defects in said structural material regardless of the relative orientation of said defects and said probe;
    a housing enclosing an air cavity;
    means for transmitting said mechanical vibrations intercepted by said receiver ring through said air cavity; and
    a receiver transducer for converting the ultrasonic vibrations transmitted through said air cavity into an electrical signal for display by said test set.

2. The probe of claim 1 further comprising a cylindrical receiver tube positioned around the periphery of said probe to convey ultrasonic vibrations from said receiver ring to said means for transmitting said mechanical vibrations through said air cavity and to enhance the structural rigidity of said probe.

3. The probe of claim 2 wherein said cylindrical receiver tube includes a separator wall extending across the inside thereof and contacting said means for transmitting said mechanical vibrations through said air cavity so that said receiver tube acts as a tuned waveguide for preferentially detecting ultrasonic vibrations of a preselected frequency.

4. A probe for detecting defects in a structural material and for actuating a test set to indicate detection of defects, said probe comprising:
    a transmitter contact for physically contacting said material in a transmitter contact region on the surface of said material;

a transmitter driver means connected to said transmitter contact for mechanically vibrating said transmitter contact so that mechanical vibrations are transmitted into said material;

a receiver contact for physically contacting said material in a receiver contact region on the surface of said material, said receiver contact region substantially surrounding said transmitter contact region so that mechanical vibrations induced by said transmitter contact in said structural material are intercepted by said receiver contact;

a receiver transducer means operatively connected to said receiver contact for converting said mechanical vibrations intercepted by said receiver contact into an output electrical signal responsive to defects in said material and for actuating said test set; and a receiver tube extending between said receiver contact and said receiver transducer means, for transmitting vibrations intercepted by said receiver contact and further for enclosing said transmitter driver means and said receiver transducer means.

5. The probe of claim 4 wherein said receiver contact has a circular ring shape, and said transmitter contact is located at the center of said circular ring receiver contact.

6. The probe of claim 4 wherein said receiver contact region has a circular ring shape, and said transmitter contact region is located at the center of said receiver contact region.

7. The probe of claim 4 wherein the length of said receiver tube between said receiver contact and said receiver transducer means is approximately equal to an odd number of quarter wavelengths of the first harmonic of said mechanical vibrations to be transmitted by said transmitter contact.

8. The probe of claim 7, additionally comprising:
a housing enclosing an air cavity; and
means for transmitting said mechanical vibrations intercepted by said receiver ring through said air cavity, wherein said receiver transducer means converts said mechanical vibrations that have been transmitted through said air cavity into an output electrical signal.

9. An ultrasonic probe for the non-destructive testing of structural materials, said probe comprising:
a receiver tube having a hollow inner bore and having a separator extending across said bore;
a transmitter assembly slidably mounted in said bore forward of said separator; and
a receiver transducer operatively connected to said separator inside said receiver tube;
wherein said separator is located along the length of said receiver tube a distance approximately equal to an odd number of quarter wavelengths of the mechanical vibrations to be detected by said receiver transducer.

10. An ultrasonic probe for the non-destructive testing of a structural material, said probe comprising:
a transmitter assembly having a transmitter button for contacting said structural material;
a receiver having a receiver ring for substantially encircling said transmitter button and for contacting said structural material, and a receiver transducer; and
a receiver tube extending between said receiver ring and said receiver transducer for transmitting vibrations intercepted by said receiver ring and further for enclosing said transmitter assembly and said receiver transducer.

11. An ultrasonic probe for the non-destructive testing of a structural material, said probe comprising:
a transmitter assembly for transmitting ultrasonic vibrations into a transmitting surface region of said structural material; and
means for receiving ultrasonic vibrations from a receiving surface region of said structural material, and wherein said receiving surface region substantially surrounds said transmitting surface region;
wherein said transmitter assembly comprises:
a transmitter button for contacting said structural material; and
means for vibrating said transmitter button at a frequency on the order of 15 kHz so that said transmitter button can transmit ultrasonic vibrations into said transmitting surface region of said structural material.

12. The ultrasonic probe of claim 11 further including means for selectively detecting the ultrasonic vibrations received by said means for receiving so that the first harmonic of the ultrasonic vibrations transmitted by said means for transmitting are selectively detected.

13. The ultrasonic probe of claim 12 wherein:
said means for selectively detecting the ultrasonic vibrations comprises a receiver tube; and
said transmitter assembly is slidably mounted inside said receiver tube and is spring biased to project from said receiver tube.

14. An ultrasonic probe for the non-destructive testing of a structural material, said probe comprising:
means for transmitting ultrasonic vibrations into a transmitting surface region of said structural material;
means for receiving ultrasonic vibrations from a receiving surface region of said structural material, said means for receiving having an omnidirectional response sensitivity to detect defects in all substantially radial directions outward from said transmitting surface region on the surface of said structural material; and
a means for selectively responding to a preselected vibration frequency, said means for selectively responding having a tuned waveguide selector for enhancing the sensitivity of said means for receiving to ultrasonic vibrations of said preselected vibration frequency.

15. A method of non-destructive testing of a structural material for use with a contacting ultrasonic probe and a test set, said method comprising the steps of:
transmitting ultrasonic vibrations into said structural material by said probe in a transmitting surface region of said structural material;
receiving ultrasonic vibrations from said structural material by said probe in a receiving surface region of said structural material, said step of receiving comprising receiving of ultrasonic vibrations in substantially all radial directions from said transmitting surface region on the surface of said structural material;
transmitting said received ultrasonic vibration through an air cavity;
converting the ultrasonic vibrations transmitted through said air cavity into a signal; and
using said signal to signal said test set with the results of said step of receiving so that defects in said structural material may be identified and located.

* * * * *